United States Patent
Paufique

(10) Patent No.: US 8,216,618 B2
(45) Date of Patent: Jul. 10, 2012

(54) **COSMETIC USE OF AN *OPHIOPOGON JAPONICUS* ACTIVE PRINCIPLE**

(75) Inventor: Jean Paufique, Objat (FR)

(73) Assignee: Societe Industrielle Limousine d'Application Biologique, Objat (FR)

( * ) Notice: Subject to any disclaimer, the term of this patent is extended or adjusted under 35 U.S.C. 154(b) by 0 days.

(21) Appl. No.: 12/990,556

(22) PCT Filed: Apr. 30, 2009

(86) PCT No.: PCT/FR2009/050802
§ 371 (c)(1), (2), (4) Date: Nov. 1, 2010

(87) PCT Pub. No.: WO2009/138702
PCT Pub. Date: Nov. 19, 2009

(65) Prior Publication Data
US 2011/0045105 A1 Feb. 24, 2011

(30) Foreign Application Priority Data
Apr. 30, 2008 (FR) ..................... 08 52941

(51) Int. Cl.
*A61K 36/00* (2006.01)
*A61K 36/8968* (2006.01)
*A61K 8/02* (2006.01)
*C12P 19/00* (2006.01)

(52) U.S. Cl. ........... 424/725; 435/72; 424/401; 424/773

(58) Field of Classification Search ........................ None
See application file for complete search history.

(56) References Cited

U.S. PATENT DOCUMENTS
2004/0052758 A1    3/2004  Paufique

FOREIGN PATENT DOCUMENTS
| FR | 2814676 A | | 4/2002 |
| JP | 62081305 A | | 4/1987 |
| JP | 08133949 A | * | 5/1996 |
| JP | 2003277285 A | | 10/2003 |
| JP | 2006347911 A | | 12/2006 |
| KR | 2005014947 A | | 2/2005 |

OTHER PUBLICATIONS

Wang et al, Quantification of fructose in dwarf lilyturf (*Ophiopogon japonicus*) and its extracts, Chinese Journal of Information on Traditional Chinese Medicine (2007) vol. 14, No. 2, pp. 47-48.*

Lin et al, Determination of *Ophiopogon japonicus* polysaccharide in plasma by HPLC with modified postcolumn fluorescence derivatization, Analytical biochemistry, (Jul. 15, 2005) vol. 342, No. 2, pp. 179-185.*

International Search Report, dated Dec. 30, 2009, from corresponding PCT application.

* cited by examiner

*Primary Examiner* — Qiuwen Mi
(74) *Attorney, Agent, or Firm* — Young & Thompson

(57) ABSTRACT

A cosmetic composition includes at least one extract that is obtained from *Ophiopogon japonicus* as an active ingredient for improving and/or reinforcing the barrier function of the skin. The reinforcing the barrier function of the skin can be for the purpose of hydration. The active ingredient can stimulate the formation of tight junctions or increase of the level of NMFs of the horny layer.

20 Claims, No Drawings

COSMETIC USE OF AN *OPHIOPOGON JAPONICUS* ACTIVE PRINCIPLE

BACKGROUND OF THE INVENTION

1. Field of the Invention

This invention relates to the cosmetic use of an extract that is obtained from *Ophiopogon japonicus* for improving and/or reinforcing the barrier function of the skin, as well as to a cosmetic skin care process designed to improve and/or reinforce the cutaneous barrier function.

The invention also relates to an active ingredient that is obtained from *Ophiopogon japonicus*, to its production process, as well as to compositions designed to improve and/or to reinforce the barrier function of the skin that comprise at least one active ingredient that is obtained from *Ophiopogon japonicus*.

2. Description of the Related Art

It is known that good hydration and preservation of the physical properties of cutaneous tissue are decisive for the appearance of the skin.

These characteristics are directly linked to the cohesion of different epidermal layers, in particular the *Stratum corneum* and the *Stratum granulosum*, which is essential for ensuring the homeostasis of the barrier function of the skin, limiting excessive losses of water, and ensuring good cutaneous hydration.

SUMMARY OF THE INVENTION

This is why this invention proposes a cosmetic active ingredient that can improve and/or reinforce the barrier function of the skin.

In particular, the purpose of this invention is the cosmetic use of an extract that is obtained from *Ophiopogon japonicus* as an active ingredient in a cosmetic composition to improve and/or reinforce the barrier function of the skin.

It is known that the intercellular junctions, in particular the locked junctions, generally called "tight junctions," play a role in the homeostasis of the barrier function of the skin.

The tight junctions are specialized intercellular junctional complexes that ensure the adhesion between the keratinocytes of the *Stratum granulosum*. They form a selective semi-permeable barrier and thus contribute to the preservation of the hydration of various epidermal layers.

The tight junctions consist of 3 categories of proteins:

Transmembrane proteins: occludins, claudins and junctional adhesion molecules (JAMs) that play a structural role by connecting the membranes of adjacent cells and ensure the cell-cell adhesion and the sealing of the tight junction, Flat or scaffold proteins, including the zonula occludens (in particular ZO-1), that link the transmembrane proteins to the actin fibers of the cytoskeleton of the cell and that engage the signaling proteins, Signaling proteins combined with tight junctions that are involved in the regulation of various cellular processes such as polarity, proliferation, and cellular differentiation.

An impairment of the tight junctions induces increased permeability of the latter and therefore an increase of the water flow toward the cutaneous surface. This can bring about an alteration of the ionic gradient of the epidermis that widely influences the various processes of the epidermal differentiation such as the synthesis and the maturation of lipids and proteins involved in the preservation of the barrier function of the skin.

This is why, to meet its objective, this invention proposes using an *Ophiopogon japonicus* extract as an active ingredient preferably acting by increasing the formation of tight junctions, in particular by stimulation of the synthesis of claudin-1 and ZO-1.

Furthermore, the *Stratum corneum* or horny layer, thanks to its special structure, ensures the cohesion of the tissue and prevents the excessive loss of water and solutes. The horny layer contains a set of intracorneocytic hydrophilic substances, the NMFs (Natural Moisturizing Factors or natural hydration factors). The NMFs, essentially composed of amino acids, urea, pyrrolidone carboxylic acid (PCA) and lactate, obtained from the degradation of the filaggrin, are equipped with highly hygroscopic properties and act like veritable biological moisturizers.

Their presence makes it possible to collect free water, to hold it within corneocytes and thus to play an important role in maintaining physical properties of the horny layer. In addition, the lactate makes it possible to maintain the acid pH of the horny layer, ensuring its integrity and its cohesion.

By retaining the water in the horny layer and by regulating the pH, the NMFs partially condition the homeostasis of the barrier function.

However, a certain number of common factors, such as age, photo-induced ageing, the daily cleaning of the skin with a harsh soap, induce a reduction in the level of NMFs within the *Stratum corneum*, which is reflected by dry skin.

Thus, this invention also proposes to use an extract from *Ophiopogon japonicus* as the active ingredient that acts preferably by increasing the NMF level of the horny layer, in particular by increasing the level of lactate and serine.

The purpose of this invention is therefore the use of an extract that is obtained from *Ophiopogon japonicus* as active ingredient in a cosmetic composition for improving and/or reinforcing the carrier function of the skin, whereby said active ingredient preferably acts by stimulating:

The formation of tight junctions, and/or

The increase in the level of NMFs of the horny layer.

Preferably, it is an active ingredient that is obtained from fructosan-rich *Ophiopogon japonicus*.

This invention thus makes it possible to ensure the cohesion of the upper layers of the epidermis.

Advantageously, it makes it possible to reduce the negligible water loss of the skin and to reduce the exfoliation of the horny layer.

Thus, by reinforcing the barrier function of the skin and by restructuring the epidermis, the active ingredient that is extracted from *Ophiopogon japonicus* according to the invention has a hydrating and restructuring cosmetic effect on the skin.

In particular, the *Ophiopogon japonicus* extract according to the invention can be used as an active ingredient in a composition for the purpose of hydration.

According to another aspect, the purpose of the invention is an *Ophiopogon japonicus* extract that is particularly suited for use as an active ingredient in a cosmetic composition to improve and/or to reinforce the barrier function of the skin. It is an extract that is obtained from *Ophiopogon japonicus*, preferably comprising at least 60% fructosans (by weight relative to the total weight of the dry extract).

The invention also relates to a particular process for obtaining such an extract.

The purpose of the invention is also a cosmetic composition that is designed to improve and/or to reinforce the barrier function of the skin, comprising an *Ophiopogon japonicus* extract as an active ingredient.

The composition according to the invention can contain 0.01 to 20% of an *Ophiopogon japonicus* extract as an active ingredient.

The administration of such a composition is preferably carried out topically.

The composition according to the invention can come in the form of creams, oil-in-water emulsions, water-in-oil or multiple emulsions, solutions, suspensions, or else powders.

Finally, the invention also has as its object a cosmetic process for skin care, designed to reinforce and/or to improve the barrier function of the skin, comprising the topical application on the skin of a composition that contains an active ingredient that is obtained from *Ophiopogon japonicus*.

DETAILED DESCRIPTION OF THE INVENTION

This invention is now described in detail.

1/Process for Obtaining an Active Ingredient According to the Invention

A useful active ingredient obtained from *Ophiopogon japonicus* according to the invention is able to be obtained by a process that comprises at least one enzymatic hydrolysis stage.

In particular, the useful active ingredient that is obtained from *Ophiopogon japonicus* according to the invention is able to be obtained by a process that comprises the following stages:

Solubilization of *Ophiopogon japonicus* tuber powders in water,
At least one enzymatic hydrolysis,
Separation of soluble and insoluble phases, and
Enzymatic inactivation by heat treatment.

These stages are common in the field of extractions of active ingredients from plants, and one skilled in the art is able to adjust the reaction parameters thereof on the basis of his general knowledge.

Enzymatic inactivation can be followed by one or more filtration and/or concentration stages. Preferably, the enzymatic inactivation is followed by at least one filtration stage and one sterilizing filtration stage.

The enzymes that are used are carbohydrases. They can be purified enzymes, mono-constituent enzymes, or else a mixture of different enzymes.

The active ingredient can be obtained in liquid form or in powder form by atomization or by freeze-drying.

2/Characterization of an Active Ingredient According to the Invention

One particularly suitable active ingredient according to the invention is an extract that is obtained from *Ophiopogon japonicus* that comprises at least 60% fructosans by weight relative to the total weight of dry material, preferably at least 80%.

The presence of fructosans in the active ingredient, in particular a content of at least 60% of the total weight of the dry material, imparts in particular its specific activity to the active ingredient according to the invention.

According to a preferred embodiment, it is an extract that is obtained from *Ophiopogon japonicus* tubers.

The active ingredient according to the invention can be defined by the characteristics disclosed below.

2-1/Dry Materials

The level of dry materials is measured by passing a sample with a given initial weight through the oven at 105° C. in the presence of sand until a constant weight is obtained.

The level of dry materials of an active ingredient that is obtained from *Ophiopogon japonicus* according to the invention is between 30 and 250 g/l, more particularly between 90 and 130 g/l.

2-2/Measurement of pH

The pH that is measured by the potentiometric method at ambient temperature leads to values of between 2.5 and 6.5, more particularly between 3.0 and 4.0.

2-3/Determination of the Fructose Content

Fructose is metered by spectrophotometry according to the method for determining ketoses (Boratynski, J., (1984), Analytical Biochemistry, 137, 2, 528-532).

The fructose level of an active ingredient that is obtained from *Ophiopogon japonicus* according to the invention is between 28 and 245 g/l, preferably between 85 and 127 g/l.

2-4/Characterization of Carbohydrates

The determination of the size of the carbohydrates of an active ingredient that is obtained from *Ophiopogon japonicus* according to the invention is carried out by high-performance liquid chromatography.

The chromatogram that is obtained shows the presence of approximately 30% of monosaccharides with molecular weight that is less than 180 Da and approximately 70% oligosaccharides and polysaccharides with a molar mass of between 180 and 7,500 Da.

The glucidic fraction of the active ingredient that is obtained from *Ophiopogon japonicus* according to the invention therefore essentially consists of oligosaccharides and polysaccharides.

2-5/Identification of the Active Fraction

The active fraction of the active ingredient that is obtained from *Ophiopogon japonicus*, acting on the ZO-1 synthesis, consists primarily of molecules with a molecular weight that is greater than 500 Da. It consists of oligofructosans and polyfructosans.

3. Evaluation of the Effect of an Active Ingredient that is Obtained from *Ophiopogon japonicus*

The active ingredient that is used for the following studies is an extract that is obtained from *Ophiopogon japonicus*, obtained by the implementation of a process that comprises the following stages:

Solubilization of *Ophiopogon japonicus* tuber powder in water at a rate of at least 50 g/l,
Enzymatic hydrolyses of carbohydrates,
Separation of soluble and insoluble phases by decanting,
Enzymatic inactivation by heat treatment,
Filtration and sterilizing filtration on a 0.22 μm filter.

The active ingredient that is obtained has the following characteristics:

Appearance: Clear liquid
Color: Yellow
Dry materials: 128.3 g/l
Fructose: 114.9 g/l (essentially in the form of oligofructosans and polyfructosans),
pH: 3.3.

The extract example is not, of course, limiting.

3.1—Effect of an Active Ingredient that is Obtained from *Ophiopogon japonicus* on the Synthesis of Claudin-1 and ZO-1

The objective of this study is to evaluate the effect of an active ingredient that is obtained from *Ophiopogon japonicus* according to the invention on the synthesis of claudin-1 and zonula occludens (ZO-1), two major proteins of the tight junctions that are very involved in the cell-cell cohesion and the homeostasis of the barrier function.

The study is carried out by Western Blot on normal human keratinocytes.

The operating protocol is as follows.

On D1, the keratinocytes are inoculated in a complete medium and incubated at 37° C.

On D5, the culture medium is eliminated and replaced by the medium that contains an active ingredient according to the invention at 0.5% and 1% or $CaCl_2$ that is used as a positive control. An untreated control is also produced.

The cells are again incubated at 37° C.

On D6, the cellular extracts are recovered.

Western Blots are then produced for metering the claudin-1 and the ZO-1.

The results that are obtained are presented in the table below:

|  | Synthesis (%) | |
| --- | --- | --- |
|  | Claudin-1 | ZO-1 |
| Untreated Control | 100 | 100 |
| $CaCl_2$ | 148 | 124 |
| Active Ingredient Obtained from *Ophiopogon japonicus* at 0.5% | 123 | 118 |
| Active Ingredient Obtained from *Ophiopogon japonicus* at 1% | 126 | 127 |

It is noted that tested at 1%, an active ingredient that is obtained from *Ophiopogon japonicus* according to the invention significantly increases the synthesis of claudin-1 by 26% and the ZO-1 by 27% by normal human keratinocytes and thus promotes the formation of tight junctions.

3.2—Effect on the ZO-1 Membrane Network

The objective of this study is to demonstrate the effect of an active ingredient that is obtained from *Ophiopogon japonicus* on the membrane network that is formed by ZO-1, one of the major components of the tight junctions.

The study is implemented by immunocytology on normal human keratinocytes after being attacked with sodium lauryl sulfate (SLS).

The operating procedure is described below.

On D1, the human keratinocytes are inoculated on the glass blades in the complete culture medium.

On D4, the keratinocytes are treated with a solution of $CaCl_2$ to make possible the formation of a network of tight junctions.

On D6, the cells are treated with a solution of SLS. At the end of the incubation, the solution of SLS is eliminated and replaced by a medium that contains 1% of an active ingredient that is obtained from *Ophiopogon japonicus* according to the invention. The cells are then incubated at 37° C.

On D8, an immuno-marking is carried out with anti-ZO-1 antibodies. The intensity of the marking on a microscope coupled with an image analysis system is then displayed.

The immunocytological results being qualitative, four levels of expression have been defined:

Absence of detection of immunoreactivity −

Low detection of immunoreactivity +

Average detection of immunoreactivity ++

High detection of immunoreactivity +++

The results that are obtained are presented in the table below:

|  | Expression of ZO-1 |
| --- | --- |
| Control that is not attacked | +++ |
| SLS-attacked control | − |
| SLS-attacked control + treated with an *Ophiopogon japonicus* extract d according to the invention at 1% | +++ |

After an SLS attack on human keratinocytes, it is noted that the ZO-1 membrane network induced by $CaCl_2$ is greatly altered.

These results show that tested at 1%, an active ingredient that is obtained from *Ophiopogon japonicus* according to the invention restores the ZO-1 synthesis and the formation of the ZO-1 membrane network of the human keratinocytes after SLS attack.

3.3 Evaluation of the Hydrating Effect 3.3.1 Effect on the NMF Level of the *Stratum corneum*

The objective of this study is to evaluate in vivo the influence of an active ingredient that is obtained from *Ophiopogon japonicus* that is formulated with 3% gel on the NMFs (Natural Moisturizing Factors or natural hydrating factors).

This study is implemented by metering lactate and serine, components of NMFs.

The metering of the lactate is done on the calves of 20 healthy female volunteers who have dry skin (hydration level of less than 50).

The metering of the serine is done on the calves of 14 healthy female volunteers who have dry skin (hydration level of less than 50).

The operating procedure is as follows.

Between D-7 and D0, the volunteers stop all application of cream on the calves.

On D0, three zones on the calves are determined for each volunteer:

An untreated zone,

A placebo zone, and

A zone that is treated with an active ingredient of *Ophiopogon japonicus* formulated at 3%.

Samples of the horny layer are taken on each of these zones.

Between D0 and D13, the volunteers apply the placebo or the active ingredient obtained from *Ophiopogon japonicus* formulated at 3% on their calves twice daily.

On D14, the three zones of the calves are determined again, and samples are taken on each zone.

On each sample taken, meterings of lactate and serine are implemented.

The results that are obtained are presented in the table below by percentage of variation relative to the placebo:

|  | Variation/Placebo (%) |
| --- | --- |
| Lactate Level | +41 |
| Serine Level | +20 |

Under the conditions of this study, it is noted that after 14 days of twice-daily applications, in comparison to the placebo, an active ingredient that is obtained from *Ophiopogon japonicus* formulated with 3% gel significantly improves the cohesion of the stratum corneum by increasing the lactate concentration of the skin by 41% and the serine concentration by 20%.

3.3.2 Study of the Long-Term Hydrating Power

This study has as its object to quantify in vivo the hydrating effect of an active ingredient that is obtained from *Ophiopogon japonicus* that is formulated with 3% gel.

The study is implemented on 25 healthy female volunteers who have dry skin on their calves (hydration level of less than 50).

The measurements are made using a corneometer that is equipped with a probe that measures quantitatively and directly the electrical capacitance of the skin. This measurement is connected directly to the state of hydration of the skin.

Between D-7 and D0, the volunteers stop all application of cream on the calves.

On D0, three zones on the calves are determined for each volunteer:

An untreated zone,
A placebo zone, and
A zone that is treated with an active ingredient that is obtained from *Ophiopogon japonicus* formulated at 3%.

The hydration level is measured on each zone.

Between D0 and D13, the volunteers apply the placebo or the active ingredient that is obtained from *Ophiopogon japonicus* formula at 3% twice daily on their calves.

On D14, the three zones of the calves are determined again, and the hydration level is measured.

The results that are obtained show that the hydration level for the zones treated with the active ingredient obtained from *Ophiopogon japonicus* formulated at 3% increases by 13% relative to the hydration level of the zones that are treated with the placebo.

Thus, under the conditions of this study, after 14 days of twice-daily applications and in comparison to the placebo, an active ingredient that is obtained form *Ophiopogon japonicus* according to the invention increases the hydration level by 13%.

3.4 Evaluation of the Effect on the Restructuring of the *Stratum corneum*

3.4.1 Effect on the Water-Insensitive Loss

The objective of this study is to quantify in vivo the effect of an active ingredient that is obtained from *Ophiopogon japonicus* formulated at 3% gel on the water-insensitive loss of the skin.

When the cutaneous barrier is damaged, disturbances appear in the regulation of the water exchanges: the water migrates more easily, which increases the water-insensitive loss.

The study is implemented on 20 healthy female volunteers who have normal skin on their arms.

The measurements of water-insensitive loss are made with a Tewameter that is equipped with a probe that measures the water vapor gradient being installed between the cutaneous surface and the ambient air. This measurement provides information on the quality of the barrier function of the skin.

The procedure of the study is described below.

Between D-7 and D0, the volunteers do not apply any cream to their arms.

On D0, three measuring zones are determined at the top of the arms:

An untreated zone,
A placebo zone,
A zone that is treated with an active ingredient that is obtained from *Ophiopogon japonicus* according to the invention and that is formulated with 3% gel. A measurement is implemented on each zone with a Tewameter. Between D0 and D13, the volunteers:

Wash the zones that are studied with an irritant soap SLS (sodium lauryl sulfate). The SLS makes it possible to increase the water losses and to amplify the restructuring effect and the barrier function of the horny layer, and Apply twice daily the placebo and the active ingredient that is obtained from *Ophiopogon japonicus* that is formulated with 3% gel.

On D14, a measurement with a Tewameter is made on each zone.

The results that are obtained show that the water-insensitive loss for the zones treated with the active ingredient that is obtained from *Ophiopogon japonicus* formulated at 3% decreases by 11% relative to the water-insensitive loss of the zones that are treated with the placebo.

Thus, under the conditions of this study, after 14 days of twice-daily applications and in comparison with the placebo, an active ingredient that is obtained from *Ophiopogon japonicus* according to the invention decreases by 11% the water-insensitive loss after repeated attacks with SLS. The active ingredient that is obtained from *Ophiopogon japonicus* therefore limits the alteration of the barrier function and thus preserves the integrity of the *Stratum corneum*.

3.4.2. Effect on the Cohesion of the *Stratum corneum*

This study has as its object to quantify in vivo the effect of an active ingredient that is obtained from *Ophiopogon japonicus* according to the invention formulated with 3% gel on the cohesion of the *Stratum corneum* by measuring an exfoliation index and the total surface area occupied by the squamae.

The exfoliation of the skin is one of the results of the loss of integrity of the horny layer.

The study is implemented on 25 healthy female volunteers who have dry skin on their calves (hydration level of less than 50).

The study of the cohesion of the *Stratum corneum* is implemented using a profilometer that is equipped with an image analyzer that makes it possible to obtain the following parameters:

Exfoliation index, and
The total surface area occupied by the squamae.

The operating procedure is indicated below.

Between D-7 and D0, the volunteers do not apply any cream to their calves.

On D0, two measurement zones are determined on the calves:

A placebo zone,
A zone that is treated with an active ingredient that is obtained from *Ophiopogon japonicus* according to the invention and formulated with 3% gel. Samples are taken on each zone studied using a D-squama.

Between D0 and D13, the volunteers apply twice daily the placebo and the active ingredient that is obtained from *Ophiopogon japonicus* and formulated with 3% gel.

On D14, the zones at the calves are determined, and sampling is carried out on each zone.

The results that are obtained are presented in the table below by variation percentage relative to the placebo:

|  | Variation/Placebo (%) |
| --- | --- |
| Exfoliation Index | −25 |
| Surface Occupied by the Squamae | −27 |

Under the conditions of this study, it is noted that after 14 days of twice-daily applications, in comparison to the placebo, an active ingredient that is obtained from *Ophiopogon japonicus*, formulated with 3% gel, leads to a reduction of 25% of the exfoliation index and 27% of the surface area that is occupied by the squamae. The active ingredient that is obtained from *Ophiopogon japonicus* thus ensures the cohesion of the horny layer by limiting excessive exfoliation.

4. Examples of Composition

This example also covers the cosmetic compositions and/or dermopharmaceutical compositions that include at least one active ingredient that is obtained from *Ophiopogon japonicus* according to this invention in different galenical forms, suitable for administration by cutaneous topical means.

These compositions can come in particular in the form of creams, oil-in-water emulsions, water-in-oil emulsions, multiple emulsions, solutions, suspensions or powders. They can be more or less fluid and have the appearance of a cream, a lotion, a milk, a serum, an ointment, a gel, a paste or a foam, or in solid form.

These compositions contain between 0.01 and 20% by weight of active ingredient(s) obtained from *Ophiopogon japonicus* according to this invention.

These compositions comprise, in addition to the active ingredient, a physiologically acceptable and preferably cosmetically acceptable medium, i.e., that does not cause sensations of discomfort that are unacceptable for the user, such as redness, gnawing pain, or tingling. This medium generally contains water.

The compositions according to the invention can contain as adjuvant at least one compound that is selected from among:
  Oils, that can be selected in particular from among the oils of silicone, linear or cyclic, volatile or non-volatile;
  Waxes, such as ozokerite, polyethylene wax, beeswax, or carnauba wax;
  Silicone elastomers;
  Surfactants, preferably emulsifiers, whether they are non-ionic, anionic, cationic, or amphoteric;
  Co-surfactants, such as linear fatty alcohols;
  Thickeners and/or solidifiers;
  Moisturizers, such as polyols like glycerol;
  Organic filters;
  Inorganic filters;
  Dyes, preservatives, feedstocks;
  Tighteners;
  Sequestering agents;
  Perfumes;
  And mixtures thereof, without this list being exhaustive.

Examples of such adjuvants are cited in particular in the CTFA Dictionary (International Cosmetic Ingredient Dictionary and Handbook published by the Personal Care Product Council).

These compositions are designed in particular to reinforce and/or to improve the barrier function of the skin.

For this purpose, the object of the invention is a cosmetic process for human skin care, designed to reinforce and/or to improve the cutaneous barrier function, comprising the topical application on the skin of a composition containing an active ingredient that is obtained from *Ophiopogon japonicus*, in particular a composition that contains between 0.01 and 20% by weight of particular active ingredient(s) obtained from *Ophiopogon japonicus* according to this invention as described in Items 1 and 2.

It is possible to cite formulations that have shown a physical stability that includes 5% of active ingredient according to the invention.

Clear Gel:
  Carbopol: 0.5% with triethanolamine: enough to make pH=6.5
  Glycerol: 10%
  Propylene glycol: 10%
  Preservative: 1.0%
  Active ingredient: 5.0%
  Water: 73.5%

Opaque Gel:
  Sepigel 305: 3%
  Lanol 99: 12%
  Preservative: 1.0%
  Active ingredient: 5.0%
  Water: 79%

Emulsified Gel:
  Montanov 202: 3.0%
  Isopropyl palmitate: 10%
  Preservative: 1.0%
  Sepigel 305: 2%
  Active ingredient: 5.0%
  Water: 79%

Non-Ionic Emulsion:
  Montane 60: 2.0%
  Montanox 60: 4.0%
  Isopropyl myristat: 8%
  Paraffin wax 130/135: 3%
  Preservative: 1.0%
  Active Ingredient: 5.0%
  Water: 77%

Anionic Emulsion:
  Stearic acid: 7.0% triethanolamine enough to make pH=8
  Ritaphyl ICS: 20%
  Preservative: 1.0%
  Active ingredient: 5.0%
  Water: 67%

Cationic Emulsion:
  Quaternium-82: 5.0%
  Cetyl alcohol: 1%
  Gemseal 60: 8%
  Cetearyl alcohol: 1%
  PEG 100 stearate: 1%
  Preservative: 1.0%
  Active ingredient: 5.0%
  Water: 78%

In addition, tests have shown the compatibility of the active ingredient with the raw materials used in cosmetics: thickeners, emulsifiers, solvents.

It is also possible to cite examples of cosmetic compositions that are designed to improve and/or to reinforce the barrier function of the skin, including the active ingredient according to the invention. The composition examples that follow are obtained by mixing different components. The quantities that are indicated are provided in percentage by weight.

4.1 Example of a Pre-Treating Serum

The formulation is as follows:

| | |
|---|---|
| DC 345 (Dow Corning): | 2% |
| BRIJ 72 (Uniquema) | 1.2% |
| DC 5200 (Dow Corning) | 2% |
| Arlatone 2121 (ICI) | 2% |
| BRIJ 721 (Uniquema) | 0.8% |
| Preservative: | 1% |
| Active ingredient according to the invention: | 3% |
| Water: | enough to make 100% |

The solution has a pH of 5.5.

4.2 Example of a Personal Care Cream

The formulation is as follows:

| | |
|---|---|
| Montanox 60 (Seppic) | 1% |
| DUB STG 30 AE (Stearinerie Dubois) | 5% |
| Diamond N (Cornelius) | 2% |
| Montane 60 (Seppic) | 2% |
| DC 345 (Dow Corning) | 8% |
| DUB IMP (Stearinerie Dubois) | 2% |
| Preservative: | 1% |
| Active ingredient according to the invention: | 3% |
| Water: | enough to make 100% |

The solution has a pH of 6.2

4.3 Example of a Thick Hydrating Milk

The formulation is as follows:

| | |
|---|---|
| DUB diol (Stearinerie Dubois) | 5% |
| Micronized Stearin P200 (Stearinerie Dubois) | 1.2% |
| Cetyl Alcohol (Stearinerie Dubois) | 1% |
| DC 345 (Dow Corning) | 8% |
| DUB PTCC (Stearinerie Dubois) | 2% |
| Gemseal 40 (Total) | 2% |
| Montanov 82 (Seppic) | 2% |
| Preservative: | 1% |
| Active ingredient according to the invention: | 3% |
| Water: | enough to make 100% |

The solution has a pH of 5.3.

The invention claimed is:

1. A cosmetic composition comprising at least one extract that is obtained from *Ophiopogon japonicus* by at least one enzymatic processing stage, comprising at least 60% fructosans by total weight of dry material, the extract comprising molecules having a molecular weight that is greater than 500 Da and consists of oligofructosans and polyfructosans, as an active ingredient for improving and/or reinforcing a barrier function of the skin.

2. The cosmetic composition according to claim 1, wherein said active ingredient stimulates a formation of tight junctions.

3. The cosmetic composition according to claim 1, wherein said active ingredient stimulates an increase of a level of NMFs of a horny layer.

4. A cosmetic composition comprising at least one extract that is obtained from *Ophiopogon japonicus* by at least one enzymatic processing stage, comprising at least 60% fructosans by total weight of dry material, the extract comprising molecules having a molecular weight that is greater than 500 Da and consists of oligofructosans and polyfructosans, as an active ingredient for improving and/or reinforcing a barrier function of the skin for a purpose of hydration.

5. The cosmetic composition according to claim 4, wherein said active ingredient stimulates a formation of tight junctions.

6. The cosmetic composition according to claim 4, wherein said active ingredient stimulates an increase of a level of NMFs of a horny layer.

7. An active ingredient comprising at least 60% fructosans by total weight of dry material, the active ingredient being molecules having a molecular weight greater than 500 Da and consisting of oligofructosans and polyfructosans, wherein said active ingredient is an extract that is obtained from *Ophiopogon japonicas* via at least one enzymatic hydrolysis stage.

8. The active ingredient according to claim 7, wherein said active ingredient is an *Ophiopogon japonicus* tuber extract.

9. The active ingredient according to claim 7, comprising:
a level of dry materials of between 30 and 250 g/l;
a pH of between 2.5 and 6.5; and
a fructose content of between 28 and 245 g/l.

10. The active ingredient according to claim 7, comprising:
a level of dry materials of between 90 and 130 g/l;
a pH of between 3.0 and 4.0; and
a fructose content of between 85 and 127 g/l.

11. A cosmetic composition that is designed to improve and/or to reinforce a barrier function of skin, containing between 0.01% and 20% of at least one active ingredient according to claim 7.

12. The cosmetic composition according to claim 11, wherein the cosmetic composition comes in a form of cream, oil-in-water emulsion, water-in-oil emulsion, multiple emulsions, solution, suspension or powder.

13. A method for improving and/or reinforcing a barrier function of the skin, comprising:
applying to a subject in need thereof an effective amount of the composition of claim 1.

14. The method according to claim 13, wherein said active ingredient stimulates a formation of tight junctions.

15. The method according to claim 13, wherein said active ingredient stimulates an increase of a level of NMFs of a horny layer.

16. A method for improving and/or reinforcing a barrier function of the skin, comprising:
hydrating the skin by applying to a subject in need thereof an effective amount of the composition of claim 4.

17. The method according to claim 16, wherein said active ingredient stimulates a formation of tight junctions.

18. The method according to claim 16, wherein said active ingredient stimulates an increase of a level of NMFs of a horny layer.

19. A method to improve and/or to reinforce a barrier function of skin, comprising:
applying to the skin a cosmetic composition containing between 0.01% and 20% of the at least one active ingredient according to claim 7.

20. The method according to claim 19, wherein the cosmetic composition comes in a form of cream, oil-in-water emulsion, water-in-oil emulsion, multiple emulsions, solution, suspension or powder.

* * * * *